United States Patent
Soltis et al.

(10) Patent No.: US 8,495,996 B2
(45) Date of Patent: *Jul. 30, 2013

(54) FUEL ALCOHOL CONTENT DETECTION VIA AN EXHAUST GAS SENSOR

(75) Inventors: Richard E. Soltis, Saline, MI (US); Gopichandra Surnilla, West Bloomfield, MI (US); Carolyn Parks Hubbard, Canton, MI (US); Kenneth John Behr, Farmington Hills, MI (US); Timothy Joseph Clark, Livonia, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 546 days.

This patent is subject to a terminal disclaimer.

(21) Appl. No.: 12/781,328

(22) Filed: May 17, 2010

(65) Prior Publication Data
US 2011/0132342 A1    Jun. 9, 2011

Related U.S. Application Data

(63) Continuation-in-part of application No. 12/631,013, filed on Dec. 4, 2009.

(51) Int. Cl.
*F02D 41/00*  (2006.01)
(52) U.S. Cl.
USPC ........................... 123/703; 123/27 GE
(58) Field of Classification Search
USPC ............. 123/1 A, 27 GE, 525, 575, 299, 479, 123/695, 693, 698, 41.86; 701/103, 108, 701/109; 60/276, 299; 73/114.69, 114.71
See application file for complete search history.

(56) References Cited

U.S. PATENT DOCUMENTS

| | | | |
|---|---|---|---|
| 4,945,882 A | 8/1990 | Brown et al. | |
| 4,953,390 A | 9/1990 | Krempl et al. | |
| 4,957,087 A | 9/1990 | Ota | |
| 4,982,709 A * | 1/1991 | Oota | 123/339.12 |
| 4,993,386 A | 2/1991 | Ozasa et al. | |
| 5,145,566 A | 9/1992 | Logothetis et al. | |
| 5,195,497 A | 3/1993 | Yoshida et al. | |
| 5,253,631 A * | 10/1993 | Curran | 123/696 |
| 5,255,661 A | 10/1993 | Nankee, II et al. | |
| 5,400,762 A | 3/1995 | Fodale et al. | |
| 5,735,245 A | 4/1998 | Kubesh et al. | |
| 5,850,824 A | 12/1998 | Seitz et al. | |
| 5,881,703 A | 3/1999 | Nankee, II et al. | |
| 6,227,033 B1 * | 5/2001 | Kainz | 73/23.32 |
| 6,644,097 B2 | 11/2003 | Davey et al. | |
| 7,209,826 B2 | 4/2007 | Abe et al. | |
| 7,826,957 B2 * | 11/2010 | Fabien | 701/103 |
| 2007/0119422 A1 * | 5/2007 | Lewis et al. | 123/431 |
| 2010/0236532 A1 * | 9/2010 | Xiao et al. | 123/677 |
| 2010/0300418 A1 * | 12/2010 | Aoki | 123/703 |

FOREIGN PATENT DOCUMENTS

JP    2011231637 A  * 11/2011

* cited by examiner

*Primary Examiner* — John T. Kwon
*Assistant Examiner* — Johnny Hoang
(74) *Attorney, Agent, or Firm* — Julia Voutyras; Alleman Hall McCoy Russell & Tuttle LLP

(57) ABSTRACT

Various systems and methods are described for an exhaust gas sensor coupled to an exhaust system of an engine. One example method comprises, during selected engine fueling conditions, alternating between applying different voltages to the sensor; and identifying an amount of alcohol in fuel injected to the engine based on sensor outputs at the different voltages.

20 Claims, 6 Drawing Sheets

FUEL ALCOHOL CONTENT DETECTION VIA AN EXHAUST GAS SENSOR

CROSS REFERENCE TO RELATED APPLICATIONS

The present application is a continuation-in-part of U.S. patent application Ser. No. 12/631,013, filed on Dec. 4, 2009, the entire contents of which are incorporated herein by reference for all purposes.

TECHNICAL FIELD

The present application relates generally to an exhaust gas sensor coupled to an exhaust system of an internal combustion engine.

BACKGROUND AND SUMMARY

Exhaust gas sensors may be operated to provide indications of various exhaust gas constituents. For example, U.S. Pat. No. 5,145,566 describes detecting water content in the exhaust gas.

The inventors herein have recognized various additional information that can be obtained from manipulation of an exhaust gas sensor, including information relating to a fuel alcohol content of a fuel burned in the engine. Thus, in one example, a method for an exhaust gas sensor coupled to an exhaust system of an engine is disclosed. The method comprises, during selected engine fueling conditions, applying different voltages to the sensor; and identifying an amount of alcohol in fuel injected to the engine based on sensor outputs at the different voltages.

Thus, in one example, the sensor outputs may be used to correlate exhaust water content to the fuel alcohol content. Specifically, responsive to application of a first and second voltages, first and second pumping currents may be generated. The first pumping current may be indicative of an amount of oxygen in a sample gas while the second pumping current may be indicative of the amount of oxygen in the sample gas plus an amount of oxygen contained in water molecules in the sample gas. As such, the amount of oxygen indicated by the first pumping current may be subtracted from the amount of oxygen plus the amount of oxygen contained in water molecules to obtain an indication of the amount of water in the exhaust gas. In this way, the fuel alcohol content may be identified based on the amount of water in the exhaust gas.

Further, the inventors have recognized that various external factors can confound the fuel alcohol content measurement when using exhaust gas sensors, such as exhaust gas oxygen sensors. For example, ambient humidity changes and/or exhaust gas recirculation (EGR) can affect the exhaust water content and thus degrade the fuel alcohol content identification. As such, to reduce disturbances on such a measurement, ambient humidity information may also be used in identifying the fuel alcohol content. In one particularly advantageous approach, the exhaust gas sensor itself, or another exhaust gas sensor, may be used to determine ambient humidity, for example, when the engine is operating without fueling (e.g., deceleration fuel shut-off), or when fuel alcohol content of the fuel is otherwise known and unchanging (e.g., during a condition other than after a fuel tank re-fill). Likewise, the sensor outputs may be used to determine alcohol content when external EGR is disabled, so that effects on exhaust water content due to varying levels of EGR are reduced.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to a method for determining an amount of alcohol in a fuel mixture (e.g., ethanol and gasoline) based on outputs from an exhaust gas sensor, such as an oxygen sensor. The exhaust gas sensor may be used to determine an amount of water in a sample gas which represents an amount of water in the exhaust gas at the time of the measurement. For example, first and second voltages may be applied to the sensor to generate first and second pumping currents (e.g., sensor outputs). Under engine non-fueling conditions such as deceleration fuel shut-off, the outputs of the sensor may be used to generate an indication of ambient humidity. During engine fueling conditions, the sensor outputs may be used with the ambient humidity to identify an amount of water in the exhaust which is proportional to the amount of alcohol in the fuel mixture. In one example, engine operating parameters such as spark timing and/or fuel injection amount may be adjusted based on the detected amount of alcohol in the fuel. In this manner, engine performance, fuel economy, and/or emissions may be maintained or improved despite the varying amounts of alcohol in the fuel.

Figure 1:
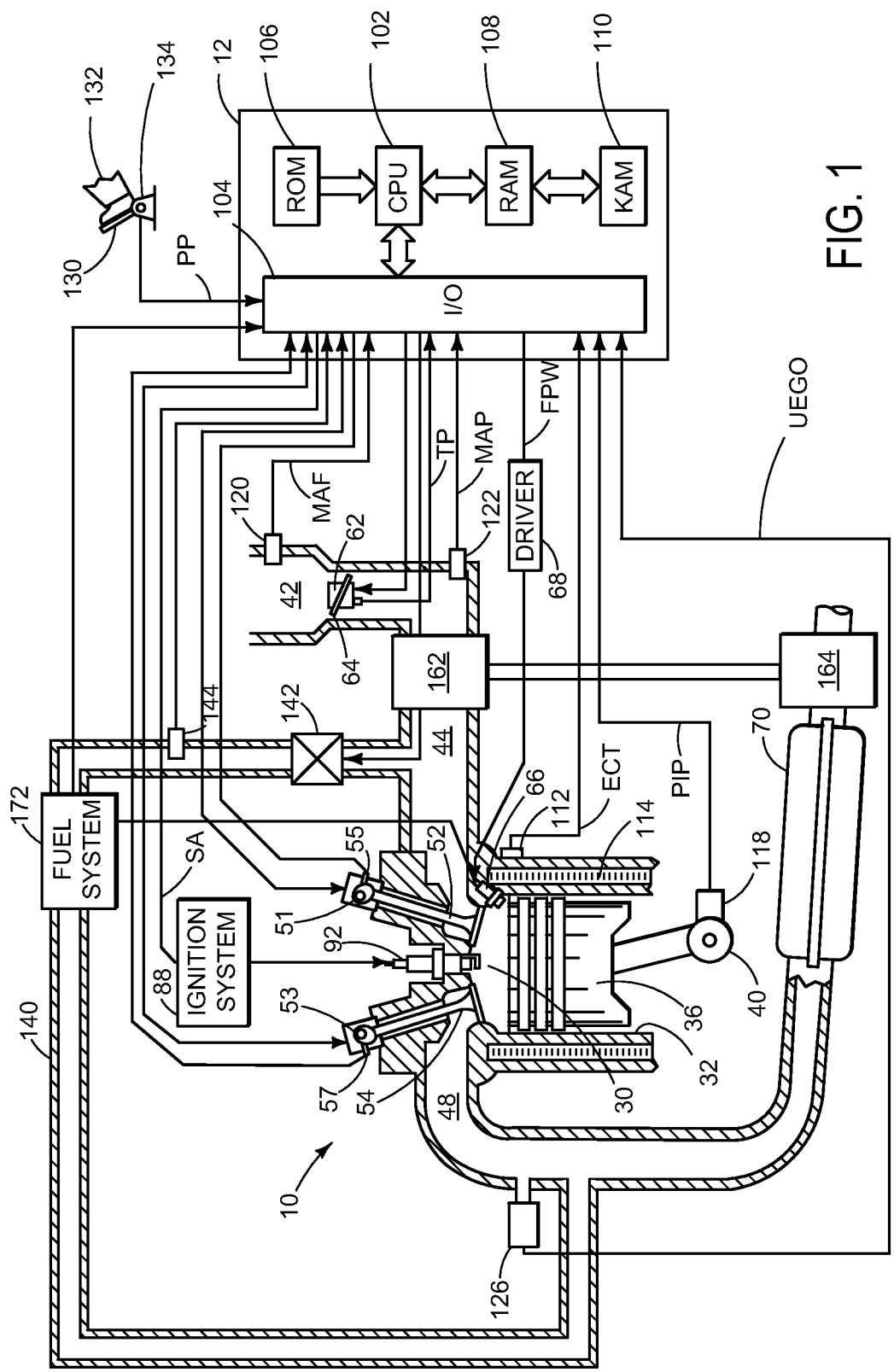
FIG. 1 shows a schematic diagram of an engine including an exhaust system and an exhaust gas sensor.

Referring now to FIG. 1, a schematic diagram showing one cylinder of multi-cylinder engine 10, which may be included in a propulsion system of an automobile, is illustrated. Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP. Combustion chamber (i.e., cylinder) 30 of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10.

Combustion chamber 30 may receive intake air from intake manifold 44 via intake passage 42 and may exhaust combustion gases via exhaust passage 48. Intake manifold 44 and exhaust passage 48 can selectively communicate with combustion chamber 30 via respective intake valve 52 and exhaust valve 54. In some embodiments, combustion chamber 30 may include two or more intake valves and/or two or more exhaust valves.

In this example, intake valve 52 and exhaust valves 54 may be controlled by cam actuation via respective cam actuation systems 51 and 53. Cam actuation systems 51 and 53 may each include one or more cams and may utilize one or more of cam profile switching (CPS), variable cam timing (VCT), variable valve timing (VVT), and/or variable valve lift (VVL) systems that may be operated by controller 12 to vary valve operation. The position of intake valve 52 and exhaust valve 54 may be determined by position sensors 55 and 57, respectively. In alternative embodiments, intake valve 52 and/or exhaust valve 54 may be controlled by electric valve actuation. For example, cylinder 30 may alternatively include an intake valve controlled via electric valve actuation and an exhaust valve controlled via cam actuation including CPS and/or VCT systems.

In some embodiments, each cylinder of engine 10 may be configured with one or more fuel injectors for providing fuel thereto. As a non-limiting example, cylinder 30 is shown including one fuel injector 66. Fuel injector 66 is shown coupled directly to cylinder 30 for injecting fuel directly therein in proportion to the pulse width of signal FPW received from controller 12 via electronic driver 68. In this manner, fuel injector 66 provides what is known as direct injection (hereafter also referred to as "DI") of fuel into combustion cylinder 30.

It will be appreciated that in an alternate embodiment, injector 66 may be a port injector providing fuel into the intake port upstream of cylinder 30. It will also be appreciated that cylinder 30 may receive fuel from a plurality of injectors, such as a plurality of port injectors, a plurality of direct injectors, or a combination thereof.

Fuel tank in fuel system 172 may hold fuels with different fuel qualities, such as different fuel compositions. These differences may include different alcohol content, different octane, different heats of vaporization, different fuel blends, and/or combinations thereof etc. The engine may use an alcohol containing fuel blend such as E85 (which is approximately 85% ethanol and 15% gasoline) or M85 (which is approximately 85% methanol and 15% gasoline). Alternatively, the engine may operate with other ratios of gasoline and ethanol stored in the tank, including 100% gasoline and 100% ethanol, and variable ratios therebetween, depending on the alcohol content of fuel supplied by the operator to the tank. Moreover, fuel characteristics of the fuel tank may vary frequently. In one example, a driver may refill the fuel tank with E85 one day, and E10 the next, and E50 the next. As such, based on the level and composition of the fuel remaining in the tank at the time of refilling, the fuel tank composition may change dynamically.

The day to day variations in tank refilling can thus result in frequently varying fuel composition of the fuel in fuel system 172, thereby affecting the fuel composition and/or fuel quality delivered by injector 66. The different fuel compositions injected by injector 166 may hereon be referred to as a fuel type. In one example, the different fuel compositions may be qualitatively described by their research octane number (RON) rating, alcohol percentage, ethanol percentage, etc.

It will be appreciated that while in one embodiment, the engine may be operated by injecting the variable fuel blend via a direct injector, in alternate embodiments, the engine may be operated by using two injectors and varying a relative amount of injection from each injector. It will be further appreciated that when operating the engine with a boost from a boosting device such as a turbocharger or supercharger (not shown), the boosting limit may be increased as an alcohol content of the variable fuel blend is increased.

Fuel system 172 may further include a fuel vapor canister with a fuel vapor purge valve. The fuel vapor canister may be a charcoal canister used to trap fuel vapors from the fuel tank, for example. When open, the fuel vapor purge valve allows the stored fuel vapors to be drawn into the cylinders for combustion with an air/fuel mixture.

Continuing with FIG. 1, intake passage 42 may include a throttle 62 having a throttle plate 64. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air provided to combustion chamber 30 among other engine cylinders. The position of throttle plate 64 may be provided to controller 12 by throttle position signal TP. Intake passage 42 may include a mass air flow sensor 120 and a manifold air pressure sensor 122 for providing respective signals MAF and MAP to controller 12.

Ignition system 88 can provide an ignition spark to combustion chamber 30 via spark plug 92 in response to spark advance signal SA from controller 12, under select operating modes. Though spark ignition components are shown, in some embodiments, combustion chamber 30 or one or more other combustion chambers of engine 10 may be operated in a compression ignition mode, with or without an ignition spark.

Exhaust gas sensor 126 is shown coupled to exhaust passage 48 upstream of emission control device 70. Sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor. Emission control device 70 is shown arranged along exhaust passage 48 downstream of exhaust gas sensor 126. Device 70 may be a three way catalyst (TWC), $NO_x$ trap, various other emission control devices, or combinations thereof. In some embodiments, during operation of engine 10, emission control device 70 may be periodically reset by operating at least one cylinder of the engine within a particular air/fuel ratio.

Further, in the disclosed embodiments, an exhaust gas recirculation (EGR) system may route a desired portion of exhaust gas from exhaust passage 48 to intake passage 44 via EGR passage 140. The amount of EGR provided to intake passage 44 may be varied by controller 12 via EGR valve 142. Further, an EGR sensor 144 may be arranged within the EGR passage and may provide an indication of one or more of pressure, temperature, and concentration of the exhaust gas. Under some conditions, the EGR system may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

Engine 10 may further include a compression device such as a turbocharger or supercharger including at least a compressor 162 arranged along intake manifold 44. For a turbocharger, compressor 162 may be at least partially driven by a turbine 164 (e.g., via a shaft) arranged along exhaust passage 48. For a supercharger, compressor 162 may be at least partially driven by the engine and/or an electric machine, and may not include a turbine. Thus, the amount of compression provided to one or more cylinders of the engine via a turbocharger or supercharger may be varied by controller 12.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; a profile ignition pickup signal (PIP) from Hall effect sensor 118 (or other type) coupled to crankshaft 40; throttle position (TP) from a throttle position sensor; and absolute manifold pressure signal, MAP, from sensor 122. Engine speed signal, RPM, may be generated by controller 12 from signal PIP.

Storage medium read-only memory 106 can be programmed with computer readable data representing instructions executable by processor 102 for performing the methods described below as well as other variants that are anticipated but not specifically listed.

As described above, FIG. 1 shows only one cylinder of a multi-cylinder engine, and each cylinder may similarly include its own set of intake/exhaust valves, fuel injector, spark plug, etc.

Figure 2:
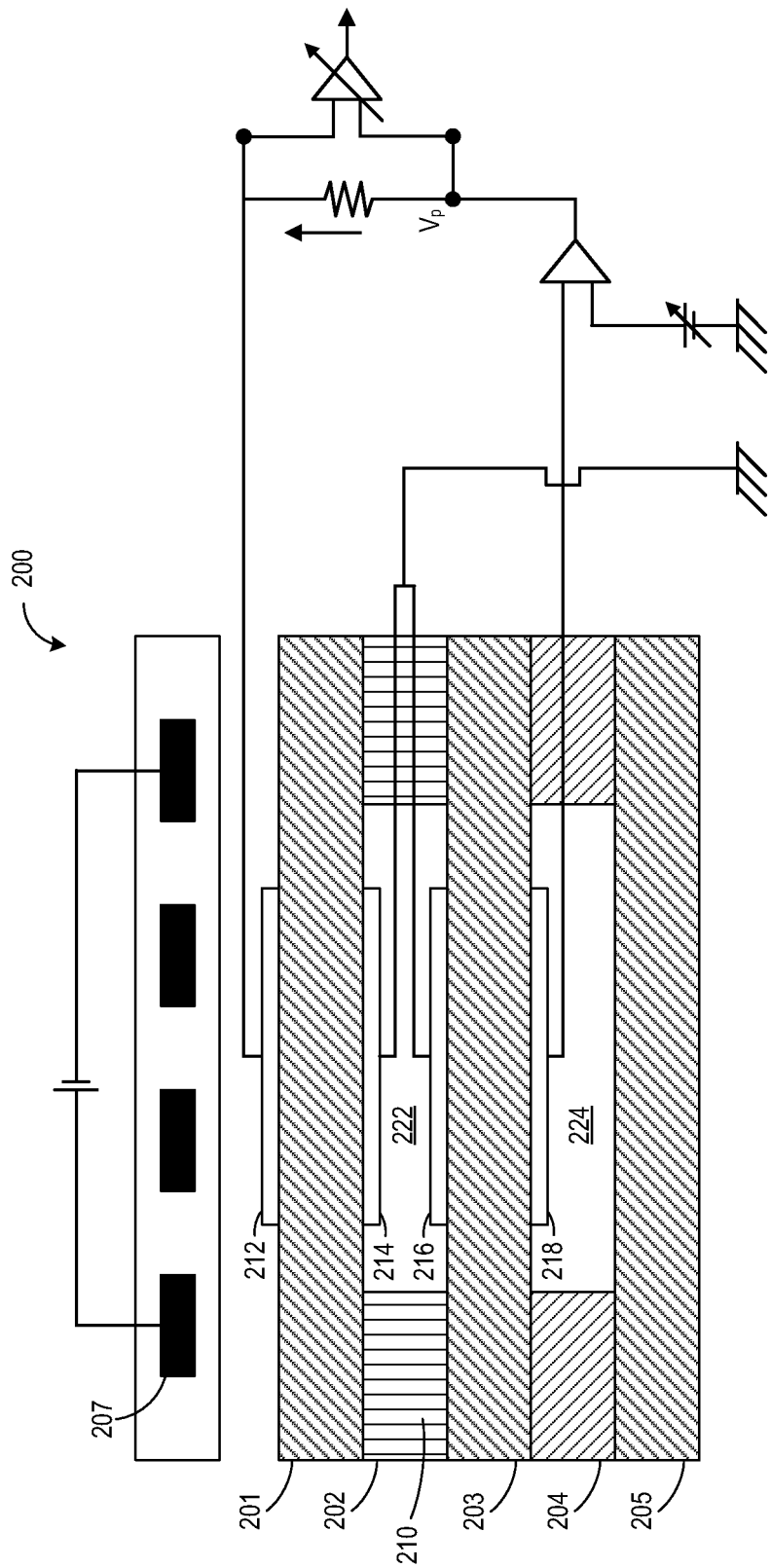
FIG. 2 shows a schematic diagram of an example exhaust gas sensor.

Next, FIG. 2 shows a schematic view of an example embodiment of a UEGO sensor 200 configured to measure a concentration of oxygen ($O_2$) in an exhaust gas stream. Sensor 200 may operate as UEGO sensor 126 of FIG. 1, for example. Sensor 200 comprises a plurality of layers of one or more ceramic materials arranged in a stacked configuration. In the embodiment of FIG. 2, five ceramic layers are depicted as layers 201, 202, 203, 204, and 205. These layers include one or more layers of a solid electrolyte capable of conducting ionic oxygen. Examples of suitable solid electrolytes include, but are not limited to, zirconium oxide-based materials. Further, in some embodiments, a heater 207 may be disposed in thermal communication with the layers to increase the ionic conductivity of the layers. While the depicted UEGO sensor is formed from five ceramic layers, it will be appreciated that the UEGO sensor may include other suitable numbers of ceramic layers.

Layer 202 includes a material or materials creating a diffusion path 210. Diffusion path 210 is configured to introduce exhaust gases into a first internal cavity 222 via diffusion. Diffusion path 210 may be configured to allow one or more components of exhaust gases, including but not limited to a desired analyte (e.g., $O_2$), to diffuse into internal cavity 222 at a more limiting rate than the analyte can be pumped in or out by pumping electrodes pair 212 and 214. In this manner, a stoichiometric level of $O_2$ may be obtained in the first internal cavity 222.

Sensor 200 further includes a second internal cavity 224 within layer 204 separated from the first internal cavity 222 by layer 203. The second internal cavity 224 is configured to maintain a constant oxygen partial pressure equivalent to a stoichiometric condition, e.g., an oxygen level present in the second internal cavity 224 is equal to that which the exhaust gas would have if the air-fuel ratio was stoichiometric. Herein, second internal cavity 224 may be referred to as a reference cell. As shown, the reference voltage is variable (e.g., between 0 and 1300 mV).

A pair of sensing electrodes 216 and 218 is disposed in communication with first internal cavity 222 and reference cell 224. The sensing electrodes pair 216 and 218 detects a concentration gradient that may develop between the first internal cavity 222 and the reference cell 224 due to an oxygen concentration in the exhaust gas that is higher than or lower than the stoichiometric level. A high oxygen concentration may be caused by a lean exhaust gas mixture, while a low oxygen concentration may be caused by a rich mixture.

A pair of pumping electrodes 212 and 214 is disposed in communication with internal cavity 222, and is configured to electrochemically pump a selected gas constituent (e.g., $O_2$) from internal cavity 222 through layer 201 and out of sensor 200. Alternatively, the pair of pumping electrodes 212 and 214 may be configured to electrochemically pump a selected gas through layer 201 and into internal cavity 222. Herein, pumping electrodes pair 212 and 214 may be referred to as an $O_2$ pumping cell.

Electrodes 212, 214, 216, and 218 may be made of various suitable materials. In some embodiments, electrodes 212, 214, 216, and 218 may be at least partially made of a material that catalyzes the dissociation of molecular oxygen. Examples of such materials include, but are not limited to, electrodes containing platinum and/or silver.

The process of electrochemically pumping the oxygen out of or into internal cavity 222 includes applying a voltage $V_p$ across pumping electrode pair 212 and 214. The pumping voltage $V_p$ applied to the $O_2$ pumping cell pumps oxygen into or out of first internal cavity 222 in order to maintain a stoichiometric level of oxygen in the cavity pumping cell. The resulting pumping current $I_p$ is proportional to the concentration of oxygen in the exhaust gas. A control system (not shown in FIG. 2) generates the pumping current signal $I_p$ as a function of the intensity of the applied pumping voltage $V_p$ required to maintain a stoichiometric level within the first internal cavity 222. Thus, a lean mixture will cause oxygen to be pumped out of internal cavity 222 and a rich mixture will cause oxygen to be pumped into internal cavity 222. Further, the output gain of the pumping current may be varied via the variable gain operational amplifier (e.g., op-amp). By varying the reference voltage and the output gain of the op-amp, the UEGO sensor may provide a higher resolution signal.

It should be appreciated that the UEGO sensor described herein is merely an example embodiment of a UEGO sensor, and that other embodiments of UEGO sensors may have additional and/or alternative features and/or designs.

Figure 3:
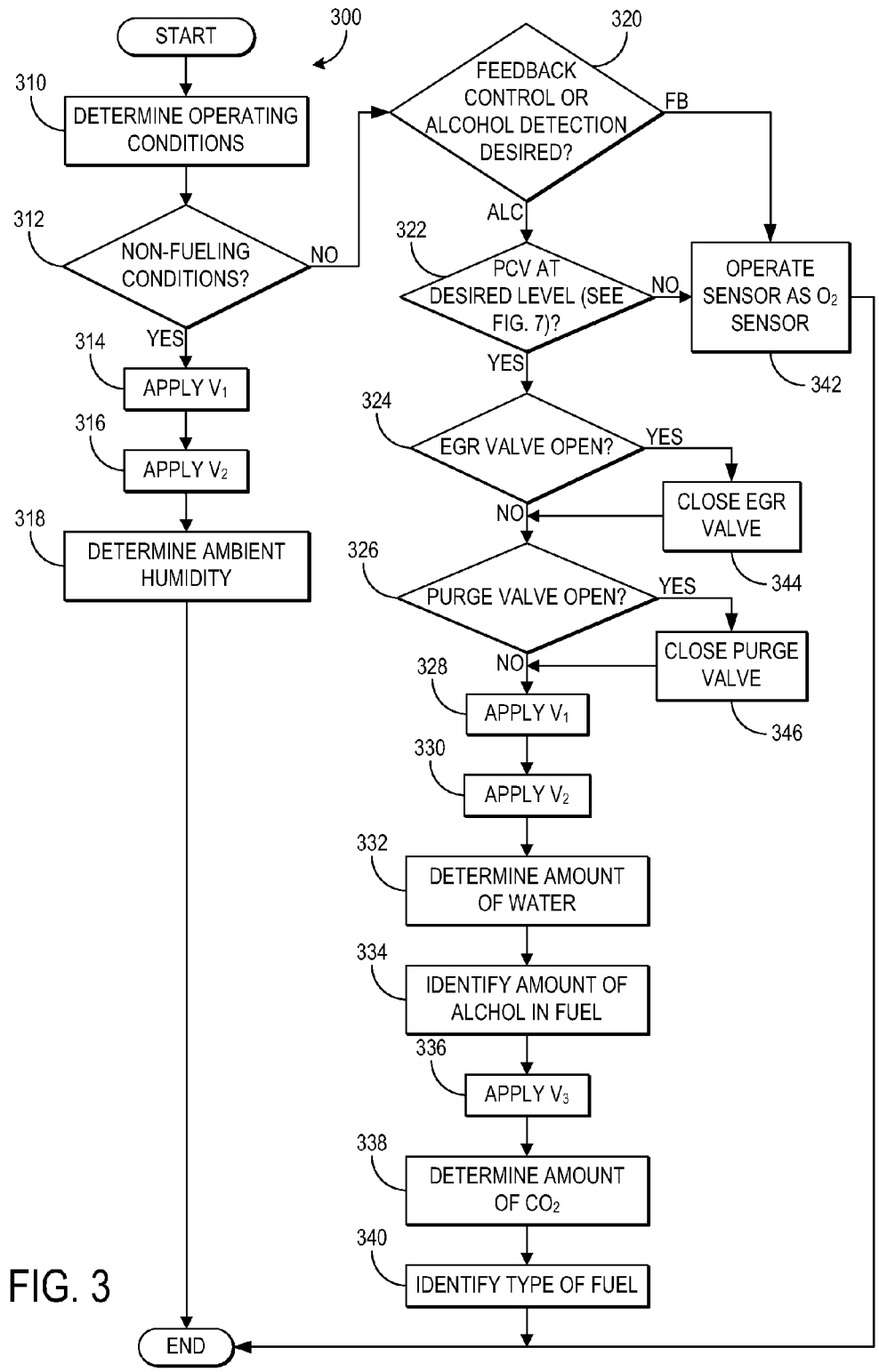
FIG. 3 shows a flow chart illustrating a routine for estimating an amount of alcohol in fuel with an exhaust gas sensor in an engine with one cylinder bank.

Moving to FIG. 3, a flow chart illustrating an estimation routine 300 for an exhaust gas sensor, such as UEGO 200 shown in FIG. 2, in an engine with one cylinder block is shown. Specifically, routine 300 determines an amount of alcohol in the fuel injected to the engine, and thus the fuel type, based on voltages applied to a pumping cell of the sensor during selected engine operating conditions.

At 310 of routine 300, engine operating conditions are determined. Engine operating conditions may include but are not limited to air-fuel ratio, amount of EGR entering the combustion chambers, and fueling conditions, for example.

Once the engine operating conditions are determined, routine 300 continues to 312 where it is determined if the engine is under non-fueling conditions. Non-fueling conditions include vehicle deceleration conditions and engine operating conditions in which the fuel supply is interrupted but the engine continues spinning and at least one intake valve and one exhaust valve are operating; thus, air is flowing through one or more of the cylinders, but fuel is not injected in the cylinders. Under non-fueling conditions, combustion is not carried out and ambient air may move through the cylinder from the intake to the exhaust. In this way, a sensor, such as a UEGO sensor, may receive ambient air on which measurements, such as ambient humidity detection, may be performed.

As noted, non-fueling conditions may include, for example, deceleration fuel shut-off (DFSO). DFSO is responsive to the operator pedal (e.g., in response to a driver tip-out and where the vehicle accelerates greater than a threshold amount). DSFO conditions may occur repeatedly during a drive cycle, and, thus, numerous indications of the ambient humidity may be generated throughout the drive cycle, such as during each DFSO event. As such, the fuel type may be identified accurately based on an amount of water in the exhaust gas despite fluctuations in humidity between drive cycles or even during the same drive cycle.

Continuing with FIG. 3, if it is determined that the engine is under non-fueling conditions such as DFSO, routine 300 continues to 314 where a first pumping voltage ($V_1$) is applied to the oxygen pumping cell of the exhaust gas sensor. The first pumping voltage may have a value such that oxygen is pumped from the cell, but low enough that oxygen compounds such as $H_2O$ (e.g., water) are not dissociated (e.g., $V_1$=450 mV). Application of the first voltage may generate an output of the sensor in the form of a first pumping current ($I_1$) that is indicative of the amount of oxygen in the sample gas. In this example, because the engine is under non-fueling conditions, the amount of oxygen may correspond to the amount of oxygen in the fresh air surrounding the vehicle.

Once the amount of oxygen is determined, routine 300 proceeds to 316 where a second pumping voltage ($V_2$) is applied to the oxygen pumping cell of the sensor. The second voltage may be greater than the first voltage applied to the sensor. In particular, the second voltage may have a value high enough to dissociate a desired oxygen compound. For example, the second voltage may be high enough to dissociate $H_2O$ molecules into hydrogen and oxygen (e.g., $V_2$=950 mV). Application of the second voltage may generate a second pumping current ($I_2$) that is indicative of the amount of oxygen and water in the sample gas. It will be understood that the term "water" in the "amount of oxygen and water" as used herein refers to the amount of oxygen from the dissociated $H_2O$ molecules in the sample gas.

The ambient humidity (e.g., absolute humidity of the fresh air surrounding the vehicle) may be determined at 318 of routine 300 based on the first pumping current and the second pumping current. For example, the first pumping current may be subtracted from the second pumping current to obtain a value indicative of the amount of oxygen from dissociated water molecules (e.g., the amount of water) in the sample gas. This value may be proportional to the ambient humidity.

On the other hand, if it is determined that the engine is not under non-fueling conditions, routine 300 of FIG. 3 moves to 320 where is it determined if feedback air-fuel ratio control based on the sensor, or alcohol detection by the sensor, is desired or to be carried out. The selection may be based on operating conditions, such as a duration since a last determination of alcohol, or whether closed loop air-fuel ratio control is enabled. For example, if feedback air-fuel ratio control is disabled, the routine may continue to determine alcohol content, whereas if feedback air-fuel ratio is commanded or enabled, the routine may continue to perform such feedback air-fuel ratio control (without determining alcohol content).

If it is determined that feedback control is desired, routine 300 moves to 342 and the sensor is operated as an oxygen (e.g., $O_2$) sensor to determine an oxygen concentration and/or air-fuel ratio of the exhaust gas and the routine ends. For example, as described herein, fuel injection is adjusted to maintain air-fuel ratio at a desired air-fuel ratio based on feedback from the oxygen sensor(s) indicating exhaust air-fuel ratio.

Figure 7:
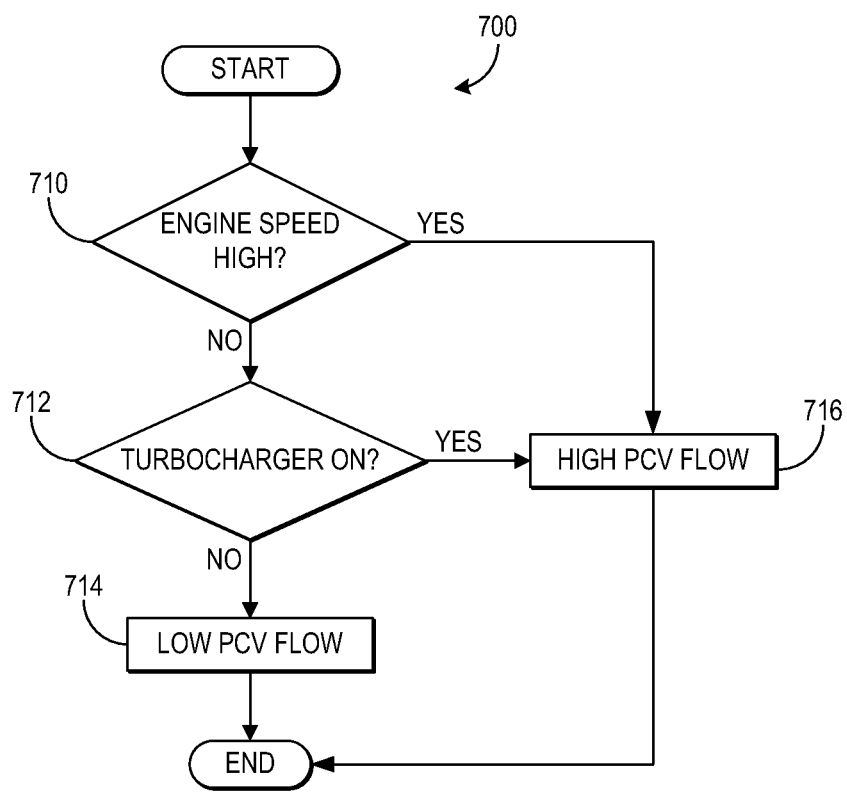
FIG. 7 shows a flow chart illustrating a routine for estimating an amount of positive crankcase ventilation.

If alcohol detection is desired, routine 300 proceeds to 322 where it is determined if positive crankcase ventilation (PCV) is at a desired level. FIG. 7 shows an example estimation routine 700 for determining an amount of PCV.

At 710 of routine 700, it is determined if the engine speed is high. If the engine speed is high, it is estimated that there may be increased PCV flow. Other example conditions include increased manifold vacuum, increased crankcase pressure, high ambient conditions, combinations thereof, etc. If the engine speed is relatively low, routine 700 proceeds to 712 where it is determined if the turbocharger is on and the engine is boosted. If the engine is under non-boosted conditions, PCV flow may be increased. On the other hand, routine 700 continues to 714 where it is determined that the flow from the PCV valve is sufficiently low.

Continuing with FIG. 3, if it is determined at 322 that the amount of PCV is above a desired level (e.g., the PCV flow is high), routine 300 moves to 342 and the sensor is operated as an oxygen sensor to determine an oxygen concentration of the exhaust gas for air-fuel control, for example, and the routine ends.

On the other hand, if PCV is at a desired level (e.g., the PCV flow is low), routine 300 continues to 324 where it is determined if the exhaust gas recirculation (EGR) valve is open. If it is determined that the EGR valve is open, routine 300 moves to 334 and the EGR valve is closed. Once the EGR valve is closed at 324 or if it is determined that the EGR valve is closed at 322, and thus the amount of EGR entering the combustion chamber is substantially zero, routine 300 proceeds to 326 where it is determined if the fuel vapor purge valve is open.

If it is determined that the fuel vapor purge valve is open, routine 300 moves to 346 and the fuel vapor purge valve is closed. Fuel vapor that is stored in the fuel vapor canister may have an alcohol content that is different than the fuel that is currently in the fuel tank. As such, fuel vapor entering the combustion chamber may affect the amount of alcohol detected by the UEGO sensor resulting in an inaccurate estimate.

Once the fuel vapor purge valve is closed at 346 or if is determined that the fuel vapor purge valve is closed at 326, routine 300 continues to 328 where a first pumping voltage ($V_1$) is applied to the exhaust gas sensor. As at 314, the first pumping voltage may pump oxygen from the oxygen pumping cell, but may have a low enough valve so as to not dissociate water (e.g., $H_2O$) molecules in the pumping cell (e.g., $V_1$=450 mV). In some examples, the first pumping voltage applied to the sensor at 328 may be the same as the first pumping voltage applied to the sensor at 314. When the first voltage is applied to the pumping cell, a first pumping current ($I_1$) may be generated. In this example, because fuel is injected to the engine and combustion is carried out, the first pumping current may be indicative of an amount of oxygen in the exhaust gas.

At 330 of routine 300, a second pumping voltage ($V_2$) is applied to the pumping cell of the exhaust gas sensor. As above, the second pumping voltage may be greater than the first pumping voltage, and the second voltage may be high enough to dissociate oxygen compounds such as water molecules. Application of the second pumping voltage across the oxygen pumping cell may generate a second pumping current ($I_2$). The second pumping current may be indicative of an amount of oxygen and water in the sample gas (e.g., oxygen that already exists in the sample gas plus oxygen from water molecules dissociated when the second pumping voltage is applied).

Once the first and second pumping currents are generated, an amount of water in the sample gas may be determined at 332 of routine 300 in FIG. 3. For example, the first pumping current may be subtracted from the second pumping current to determine a value that corresponds to an amount of water.

Figure 5:
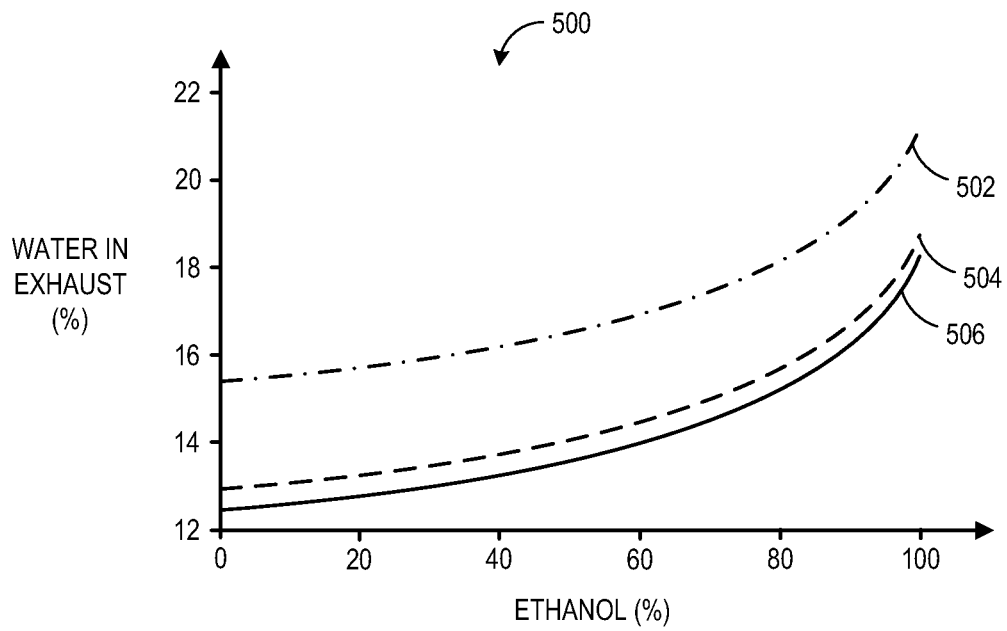
FIG. 5 shows a graph demonstrating a relationship between water in exhaust gas and ethanol.

The amount of alcohol in the fuel may be identified at 334 of routine 300. For example, the amount of water in the exhaust gas may be proportional to an amount of alcohol (e.g., a percent of ethanol) in the fuel injected to the engine. Because ambient humidity may also contribute to an amount of water in the exhaust gas, the ambient humidity determined at 318 may be subtracted from the amount of water determined at 330. In some embodiments, the computer readable storage medium of the control system receiving communication from the sensor may include instructions for identifying the amount of alcohol. For example, graph 500 in FIG. 5 shows examples of the relationship between water after combustion (e.g., percent of water in exhaust gas) and the percent of ethanol in the fuel that may be stored on the computer readable storage medium in the form of a lookup table, for example. The solid curve 506 of graph 500 shows the percent of water in the exhaust gas when there is zero ambient humidity. The dashed curve 504 and dashed/dotted curve 502 show the percent of water in the exhaust gas when there is 0.5 mol % and 3.5 mol % water, respectively, due to ambient humidity. As demonstrated by graph 500, as the amount of ethanol in the fuel increases, the amount of water in the exhaust gas increases.

At 336 of routine 300, a third pumping voltage ($V_3$) is applied to the pumping cell of the exhaust gas sensor. The third pumping voltage may be greater than the first pumping voltage, and the second voltage may be high enough to dissociate oxygen compounds such as water and carbon dioxide ($CO_2$) (e.g., $V_3$=1.2 V). Application of the third pumping voltage across the oxygen pumping cell may generate a third pumping current ($I_3$). The third pumping current may be indicative of an amount of oxygen, water, and carbon dioxide in the sample gas (e.g., oxygen that already exists in the sample gas plus oxygen from $H_2O$ molecules dissociated when the second pumping voltage is applied plus oxygen from $CO_2$ molecules dissociated when the third pumping voltage is applied).

Once the third pumping current is generated, an amount of carbon dioxide in the sample gas may be determined at 338 of routine 300 in FIG. 3. For example, the first and second pumping currents may be subtracted from the third pumping current to determine a value that corresponds to an amount of carbon dioxide.

Finally, at 340 of routine 300, the type of fuel may be identified based on the amount of carbon dioxide determined at 338. For example, carbon content may be identified once the amount of carbon dioxide is determined. Once the carbon content is identified, the type of fuel may be determined (e.g., ethanol, methanol, CNG, etc.). Further, by determining a total amount of oxygen using pumping currents which dissociate water an carbon dioxide, an alcohol concentration may be determined with a higher signal to noise ratio than using only pumping currents which dissociate water.

Thus, based on sensor outputs (e.g., pumping currents) generated responsive to voltages applied to the oxygen pumping cell of the exhaust gas sensor during engine fueling and non-fueling conditions, amounts of water and carbon dioxide in the exhaust gas may be determined. In this manner, an accurate indication of the amount alcohol (e.g., percent ethanol) in the fuel as well as the type of fuel (e.g., ethanol, methanol, etc.) may be identified. Further, once the fuel type is determined, various engine operating parameters may be adjusted to maintain engine and/or emissions efficiency, as will be described in detail below.

While FIG. 3 shows adjusting various operations to improve fuel alcohol content determination, such as reducing or stopping EGR and/or purge vapor flow, the routine may be adjusted to take a more passive approach and check and wait for such conditions before determining fuel alcohol content. In this case, the "YES" determination from each of 324 and 326 may also lead to 342. For example, the routine may determine whether fuel vapor purge flow is less than a threshold amount. If so, the alcohol determination may be carried out. The flow may be reduced below the threshold by actively closing the purge valve, or waiting for the purge flow to fall below the threshold purge level. A similar approach may be used with EGR via an EGR threshold level.

Figure 4:
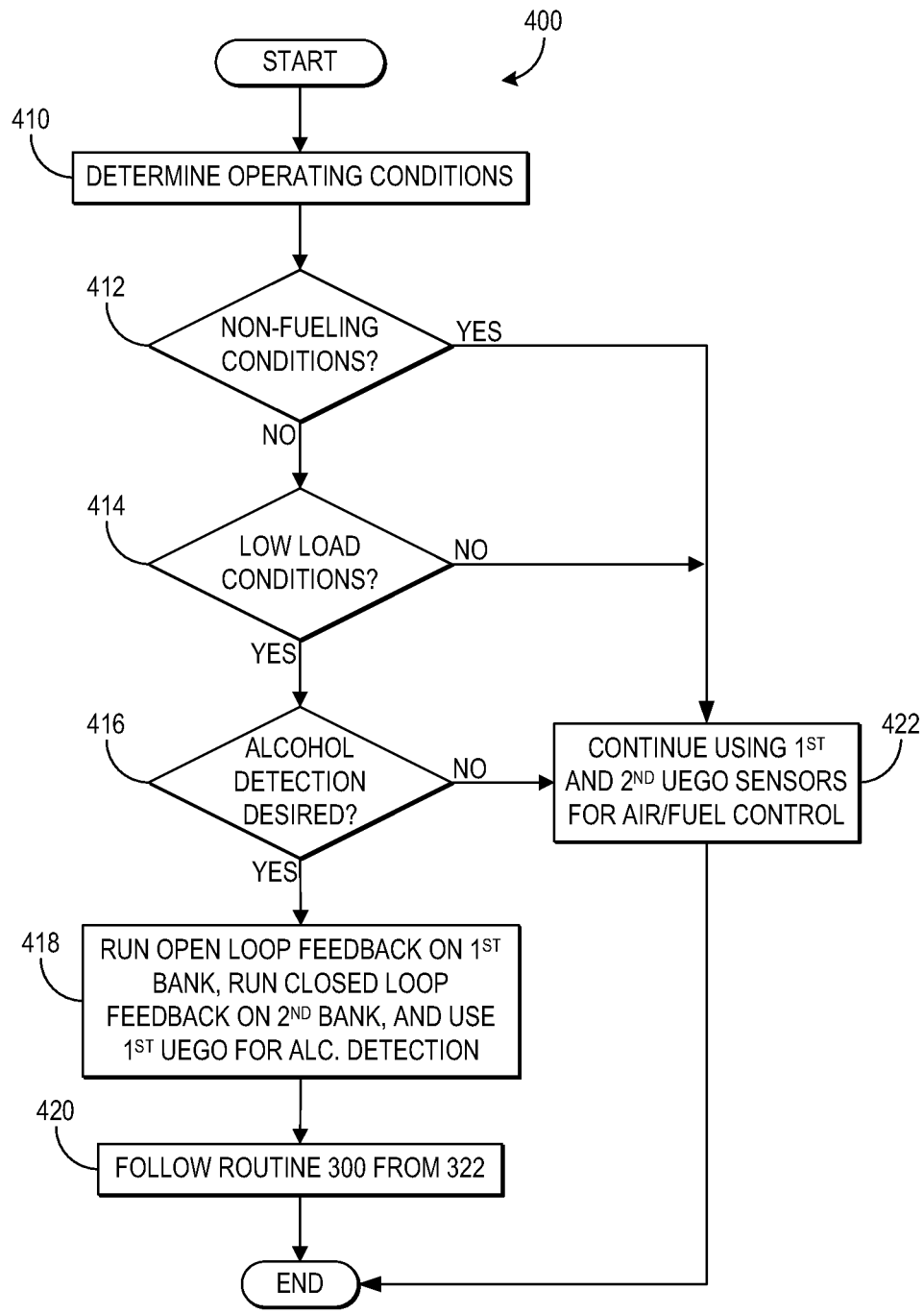
FIG. 4 shows a flow chart illustrating a routine for estimating an amount of alcohol in fuel with an exhaust gas sensor in an engine with two cylinder banks.

Additionally, even when feedback air-fuel control is to be carried out, a first oxygen sensor (e.g., a first UEGO sensor) may be used for feedback control, and a second oxygen sensor (e.g., a second UEGO sensor) may be used for determining the fuel alcohol amount. For example, if the engine has two cylinder banks, each with an exhaust UEGO sensor, one UEGO sensor may be used to control the air-fuel ratio of each bank (even though the sensor does not experience exhaust gas from one of the banks) on the assumption that the sensor is at least indicative of the air-fuel ratio of both banks, whereas the UEGO of the other bank is operated to determine fuel alcohol content. Alternatively, the first UEGO sensor may be upstream of the second UEGO sensor in the same exhaust stream. Again, the engine air-fuel ratio may be controlled by adjusting fuel injection based on the upstream UEGO, and the downstream UEGO may be used to measure fuel alcohol content. FIG. 4 shows a flow chart illustrating an estimation routine 400 for an exhaust gas sensor, such as UEGO 200 shown in FIG. 2, in an engine with two cylinder blocks and corresponding UEGO sensors for each cylinder block. Specifically, routine 400 determines an amount of alcohol in the fuel injected to the engine, and thus the fuel alcohol content, based on voltages applied to a pumping cell of the sensor during selected engine operating conditions.

At 410 of routine 400, engine operating conditions are determined. As described above, engine operating conditions may include but are not limited to air-fuel ratio, amount of EGR entering the combustion chambers, and fueling conditions, and engine load, for example.

Once the engine operating conditions are determined, routine 400 continues to 412 where it is determined if the engine is under non-fueling conditions. If the engine is under non-fueling conditions such as DFSO, for example, routine 400 moves to 422 and the first and second UEGO sensors corresponding to the first and second cylinder banks each operate to indicate ambient humidity, as described above herein. However, in this example, as both sensors may be used to sense ambient humidity, the routine may average the ambient humidity determined from each sensor to reduce the effect of noise in the signals and thereby reduce estimation errors.

On the other hand, if it is determined that the engine is under fueling conditions, and thus an alcohol content of the fuel may be determined, routine 400 proceeds to 414 where it is determined if the engine is under low load conditions. For example, during low load conditions when a relatively smaller amount of fuel and air are used for combustion, closed loop feedback of one of the cylinder blocks may be turned off with a relatively low effect on emissions. If it is determined that the engine is not under low load conditions, routine 400 moves to 424.

If it is determined that the engine is operating under low load conditions, routine 400 continues to 416 where it is determined if alcohol detection is desired. As described above, the selection may be based on operating conditions such as a duration since a last determination of alcohol. If alcohol detection is not desired, routine 400 moves to 424 and the first and second UEGO sensors continue operation for air-fuel ratio control with closed loop feedback.

If it is determined that alcohol detection is desired, routine 400 proceeds to 418 and fuel injection to the first cylinder bank is determined independent of the first UEGO sensor (but may be adjusted based on other air-fuel sensors coupled in the second bank, such as a HEGO sensor coupled downstream of an emission control device coupled exclusively to the first cylinder group) in an open loop fashion. Further fuel injection to the second bank may be based on feedback from the second UEGO sensor (as well as based on a HEGO sensor coupled downstream of an emission control device coupled exclusively to the second cylinder group). Further still, feedback from the second UEGO sensor used for air-fuel control of the second bank may also be provide feedback to fuel injection to the first cylinder bank. As such, feedback fuel injection adjustments to both cylinder banks is based on the second UEGO sensor, and independent of the first UEGO sensor, as the first UEGO sensor is operated to identify water content, and thus alcohol content, of the injected fuel. Since the same fuel is injected to both banks, such an approach enables determination of fuel alcohol content while accurately controlling fuel injection to both banks based on feedback control.

Routine 400 then continues to 420 and routine 300 of FIG. 3 is carried out from 322 for determining the fuel alcohol content.

Thus, in one example, a method may be provided for an engine with a first and second UEGO sensor, where during selected engine fueling conditions, alternating first, second, and third voltages are applied to the first UEGO sensor (and a fuel alcohol amount is determined based on the sensor outputs resulting form the first and second voltages), and at the same time, the fuel injection into the engine (both banks) is adjusted to maintain a desired air-fuel ratio based on feedback from the second UEGO sensor. Such operation may then be switched between the first and second UEGO sensors in order to monitor whether proper determination of fuel alcohol content has been achieved, and thus to monitor performance of the first and/or second UEGO sensor in identifying fuel alcohol content.

It should be appreciated that the different engine cylinder banks may operate in different modes at the same time. For example, one cylinder group may be in a DFSO mode, whereas the other cylinder group is carrying out combustion. As such, a UEGO sensor coupled exclusively to the DFSO cylinders may provide an indication of ambient humidity, whereas the UEGO sensor coupled exclusively to cylinders carrying out combustion (but with no EGR and no fuel vapor purge) can determine the water content of the fuel and ambient air, and thus from these two readings, the alcohol content of the fuel is determined.

Figure 6:
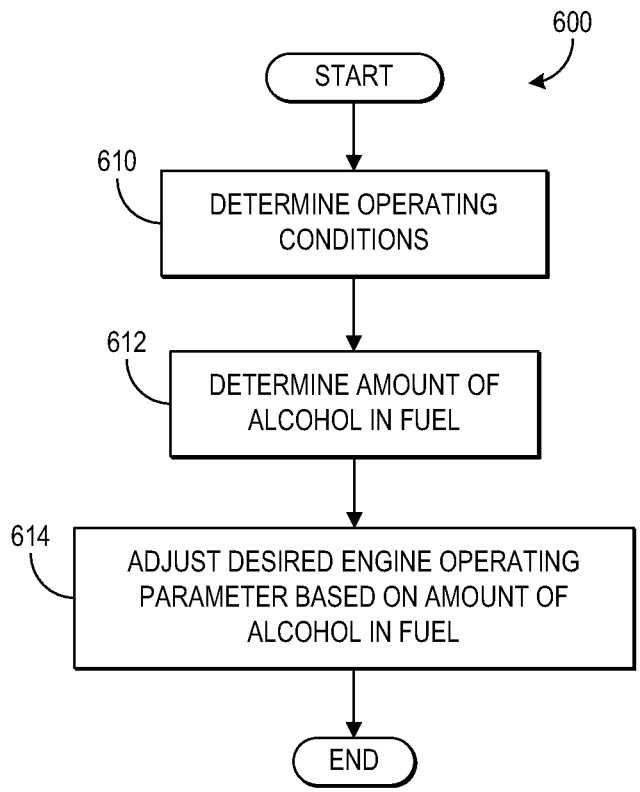
FIG. 6 shows a flow chart illustrating a routine for controlling an engine based on an exhaust gas sensor.

Referring now to FIG. 6, a flow chart depicting a general control routine 600 for adjusting engine operating parameters based on an amount of alcohol in fuel injected to the engine is shown. Specifically, one or more engine operating parameters may be adjusted corresponding to a change in the amount of alcohol in the fuel. For example, fuels containing different amount of alcohol may have different properties such as viscosity, octane number, latent enthalpy of vaporization, etc. As such, engine performance, fuel economy, and/or emissions may be degraded if one or more appropriate operating parameters are not adjusted.

At 610 of routine 600, engine operating conditions are determined. Engine operating conditions may include, for example, air-fuel ratio, fuel injection timing, and spark timing. For example, the ratio of air to fuel which is stoichiometric may vary for varying types (e.g., 14.7 for gasoline, 9.76 for E85) and fuel injection timing and spark timing may need to be adjusted based on the fuel type.

Once the operating conditions are determined, the amount of alcohol in the fuel mixture is determined at 612 of routine 600. As described above, the fuel type may be determined based on outputs from an exhaust gas sensor such as a UEGO sensor. After the fuel type is known, routine 600 proceeds to 614 where, under selected operating conditions such as cold start or transient fueling conditions, one or more desired operating parameters are adjusted based on the amount of alcohol in the fuel. For example, the system may adjust the stoichiometric air-fuel ratio based on the amount of alcohol in the fuel. Further, feedback air-fuel ratio control gains may be adjusted based on the amount of alcohol in the fuel. Further still, the desired air-fuel ratio during cold starting may be adjusted based on the amount of alcohol in the fuel. Further still, spark angle (such as spark retard) and/or boost levels may be adjusted based on the amount of alcohol in the fuel.

In some embodiments, for example, the timing and/or amount of the fuel injection in one or more cylinders may be adjusted. For example, if it is determined that the amount of alcohol in the fuel is increased (e.g., from 10% ethanol to 30% ethanol) during cold start conditions, the amount of fuel injected to the engine may be increased.

As another example, spark timing may be adjusted based on the detected amount of alcohol in the fuel. For example, if the detected percentage of alcohol is lower than previously detected (e.g., from 85% ethanol to 50% ethanol), the spark timing may be retarded in order to achieve a higher engine output or boost without knock.

Thus, various engine operating parameters may be adjusted during selected operating conditions based on a detected amount of alcohol in the fuel injected to the cylinders of the engine. In this manner, engine and/or emissions efficiency as well as fuel economy may be maintained or improved.

Note that the example control and estimation routines included herein can be used with various engine and/or vehicle system configurations. The specific routines described herein may represent one or more of any number of processing strategies such as event-driven, interrupt-driven, multi-tasking, multi-threading, and the like. As such, various acts, operations, or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated acts or functions may be repeatedly performed depending on the particular strategy being used. Further, the described acts may graphically represent code to be programmed into the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application.

Such claims, whether broader, narrower, equal, or different in scope to the original claims, also are regarded as included within the subject matter of the present disclosure.

The invention claimed is:

1. A method for an exhaust gas sensor coupled to an engine exhaust system, comprising:
    during selected non-fueling conditions, applying different voltage values to the exhaust gas sensor and detecting ambient humidity based on sensor outputs at the different voltage values; and
    during selected fueling conditions, applying different voltage values to the exhaust gas sensor and identifying an amount of alcohol in fuel injected to the engine based on sensor outputs at the different voltage values and based on the detected ambient humidity.

2. The method of claim 1 wherein the selected fueling conditions include the engine operating with a fuel vapor purging amount below a threshold amount.

3. The method of claim 1 wherein the selected fueling conditions include the engine operating with an EGR amount below a threshold amount.

4. The method of claim 1 wherein the selected fueling conditions include the engine operating with a PCV amount below a threshold amount.

5. The method of claim 1 wherein the different voltage values are successively and alternatively applied.

6. The method of claim 1, wherein the selected non-fueling conditions include deceleration fuel shut-off.

7. A method for an exhaust gas sensor coupled to an engine exhaust system, comprising:
    during selected non-fueling conditions, applying first and second voltage values to the exhaust gas sensor and generating an indication of ambient humidity based on sensor outputs at the first and second voltage values;
    during selected fueling conditions, applying the first and second voltage values as well as a third voltage value to the exhaust gas sensor, and identifying an amount of alcohol in fuel injected to the engine based on sensor outputs at the first and second voltage values and the ambient humidity; and
    identifying fuel type of fuel injected to the engine based on sensor outputs at the first, second, and third voltage values and the ambient humidity.

8. The method of claim 7, further comprising generating numerous indications of the ambient humidity throughout a drive cycle.

9. The method of claim 7, wherein the first voltage value is less than the second voltage value and the second voltage value is less than the third voltage value, wherein the second voltage value dissociates water molecules and the first voltage value does not, and wherein the third voltage value dissociates both water molecules and $CO_2$ molecules and the first and second voltage values do not.

10. The method of claim 7, wherein generating the indication of ambient humidity comprises subtracting a first pumping current generated by application of the first voltage value from a second pumping current generated by application of the second voltage value.

11. The method of claim 7, wherein the selected fueling conditions include one or more of fuel vapor purging below a threshold amount, EGR below a threshold amount, and PCV below a threshold amount.

12. A method for a first and second exhaust gas sensor coupled to an exhaust system of an engine, comprising:
    during an engine non-fueling mode:
        generating an indication of ambient humidity with the first and second sensors;
    during a first engine fueling mode:
        applying different voltage values to the first sensor and identifying an amount of alcohol in fuel injected to the engine based on sensor outputs of the first sensor at the different voltage values and the ambient humidity, and adjusting fuel injection in response to feedback from the second exhaust gas sensor to maintain a desired air-fuel ratio; and
    during a second engine fueling mode:
        maintaining voltages applied to the first and second sensors and adjusting fuel injection in response to feedback from the first and second sensors to maintain desired air-fuel ratio.

13. The method of claim 12, wherein the first engine fueling mode includes engine operation with one or more of fuel vapor purging below a threshold amount, EGR below a threshold amount, and PCV below a threshold amount.

14. The method of claim 12 further comprising, during the first engine fueling mode, identifying a fuel type of fuel injected to the engine based on the sensor outputs of the first sensor at the different voltage values and the ambient humidity.

15. The method of claim 12, wherein generating the indication of ambient humidity with the first and second sensors comprises generating a first indication of ambient humidity at the first sensor by applying first and second voltage values to the first sensor and generating a second indication of ambient humidity at the second sensor by applying first and second voltage values to the second sensor.

16. The method of claim 15, wherein generating the indication of ambient humidity with the first and second sensors further comprises averaging the first and second indications of ambient humidity.

17. A method for an engine, comprising:
    identifying fuel alcohol content of a fuel injected to the engine in response to water content in an exhaust system of the engine and ambient humidity, the water content generated from an oxygen sensor operating with different cell potentials during selected engine fueling conditions and from an indication of ambient humidity generated by the oxygen sensor operating with different cell potentials during selected non-fueling conditions.

18. The method of claim 17, wherein identifying the fuel alcohol content of the fuel injected to the engine in response to the water content in the exhaust system of the engine and the ambient humidity comprises subtracting the ambient humidity from the water content.

19. A method for an engine, comprising:
identifying fuel type of a fuel injected to the engine in response to water and CO2 content in an exhaust system of the engine and ambient humidity, the water and CO2 content generated from an oxygen sensor operating with different cell potentials during selected engine fueling conditions and from an indication of ambient humidity generated by the oxygen sensor operating with different cell potentials during selected non-fueling conditions.

20. The method of claim 19, further comprising:
generating the water content by adjusting a water content measured by the oxygen sensor based on the ambient humidity; and
generating the CO2 content based on the adjusted water content.

* * * * *